(12) United States Patent
Oseka

(10) Patent No.: US 11,324,740 B2
(45) Date of Patent: May 10, 2022

(54) USE OF AGONISTS OF TYPE-2 DOPAMINERGIC RECEPTORS IN TREATMENT OF CONDITIONS CAUSED BY ELEVATED VASCULAR ENDOTHELIAL GROWTH FACTOR LEVELS

(71) Applicant: Maciej Oseka, Duchnów (PL)

(72) Inventor: Maciej Oseka, Duchnów (PL)

( * ) Notice: Subject to any disclaimer, the term of this patent is extended or adjusted under 35 U.S.C. 154(b) by 0 days.

(21) Appl. No.: 16/836,168

(22) Filed: Mar. 31, 2020

(65) Prior Publication Data
US 2020/0222387 A1 Jul. 16, 2020

Related U.S. Application Data

(62) Division of application No. 16/060,517, filed as application No. PCT/IB2016/057483 on Dec. 9, 2016, now abandoned.

(51) Int. Cl.
*A61K 31/48* (2006.01)
*A61P 27/02* (2006.01)
*A61K 9/00* (2006.01)

(52) U.S. Cl.
CPC ............ *A61K 31/48* (2013.01); *A61K 9/0053* (2013.01); *A61P 27/02* (2018.01)

(58) Field of Classification Search
CPC .......................... A61K 31/4355; A61P 27/02
See application file for complete search history.

(56) References Cited

U.S. PATENT DOCUMENTS

2010/0130569 A1* 5/2010 Okamoto ................ A61P 25/02
514/367

FOREIGN PATENT DOCUMENTS

| EP | 2156833 A1 | 2/2010 |
| WO | 2011/069051 A1 | 6/2011 |

OTHER PUBLICATIONS

Cheung, Gemmy Chui Ming, et al., Anti-VEGF Therapy for Neovascular AMD and Polypoidal Choroidal Vasculopathy, Asia-Pacific Journal of Ophthalmology, vol. 6, No. 6, Nov./Dec. 2017, www.apjo.org, pp. 527-534.
Jama, VEGF Inhibitors for AMD and Diabetic Macular Edema, From The Medical Letter on Drugs and Therapeutics, Clinical Review & Education, http://jama.jamanetwork.com, Nov. 24, 2015, vol. 314, No. 20, pp. 2184-2185.
Meyer, Ch, et al., Preclinical Aspects of Anti-VEGF Agents For The Treatment Of Wet AMD: ranibizumab and bevacizumab, Macmillan Publishers Limited, Eye (2011) 25, pp. 661-672.
Urias, et al., NovelTherapeutic Targets in Diabetic Macular Edema: Beyond VEGF, Urias, E.A., Vision Research (2017), http://dx.doi.org/10.1016/j.visres.2017.06.015, 7 pages.
PCT International Search Report and Written Opinion dated Mar. 22, 2017 from Application No. PCT/IB2016/057483, 10 pages.
Martin, Daniel F. et al., "Ranibizumab and Bevacizumab for Treatment of Neovascular Age-related Macular Degeneration", Opthalmology, vol. 127, No. 4, Supplement, pp. S136-S145 (2020).
Newman-Tancredi, Adrian et al., Differential Actions of Antiparkinson Agents at Multiple Classes of Monoaminergic Receptor. III. Agonist and Antagonist Properties at Serotonin, 5-HT$_1$ and 5-HT$_2$, Receptor Subtypes, The Journal of Pharmacology and Experimental Therapeutics, vol. 303, No. 2, pp. 815-822 (2002).
Sangroongruangsri, Sermsiri et al., "Comparative efficacy of bevacizumab ranibizumab, and aflibercept for treatment of macular edema secondary to retinal vein occlusion: A systematic review and network meta-analysis", Expert Review of Clinical Pharmacology, 40 pages (2018). DOI: 10.1080/17512433.2018.1507735.
Wells, John A. et al., "Aflibercept, Bevacizumab, or Ranibizumab for Diabetic Macular Edema", N Engl J Med., 372(13):1193-1203 (2015). DOI:10.1056/NEJMoa1414264.
Zhao, Yue et al., "The role of anti-vascular endothelial growth factor (anti-VEGF) in the management of proliferative diabetic retinopathy", Drugs in Context, 7: 212532 (2018). DOI: 10.7573/dic.212532.

* cited by examiner

*Primary Examiner* — Marcos L Sznaidman
(74) *Attorney, Agent, or Firm* — Wenderoth, Lind & Ponack, L.L.P.

(57) ABSTRACT

A method is provided for using of type-2 dopaminergic receptor agonists, for example, cabergoline, in treatment of eye diseases caused by an elevated level of vascular endothelial growth factor (VEGF), particularly in treatment or prevention of diseases of an eye retina resulting from an increase in permeability of blood vessels and their angiogenesis using cabergoline, a dopaminergic D2 receptor agonist.

8 Claims, No Drawings

USE OF AGONISTS OF TYPE-2 DOPAMINERGIC RECEPTORS IN TREATMENT OF CONDITIONS CAUSED BY ELEVATED VASCULAR ENDOTHELIAL GROWTH FACTOR LEVELS

The present invention relates to the use of type-2 dopaminergic receptor agonists in treatment of eye diseases caused by an elevated level of vascular endothelial growth factor (VEGF), particularly in treatment or prevention of retinal disorders resulting from an increase in permeability of blood vessels and their angiogenesis.

BACKGROUND OF THE INVENTION

Eye diseases, in which an increase in permeability of blood vessels and their angiogenesis occur, include a multitude of diseases, mainly of the retina, such as diabetic macular edema, diabetic retinopathy, age-related macular degeneration, retinal artery occlusion or retinal vein occlusion.

Diabetic macular edema (DME) develops in patients with prolonged diabetes and more advanced presentation of diabetic retinopathy. It occurs in about 14% of diabetics. The frequency of DME occurrence is dependent on stage of retinopathy and diabetes type and duration. After 25 years of diabetes DME occurs in about 30% of patients with type 1 and type 2 diabetes treated with insulin and in about 15% of patients with type 2 diabetes treated with oral anti-diabetic medication. Diabetic macular edema is defined by a presence of liquid or hard exudates within 1 dd (disc diameter of the optic nerve) from the center of the macula.

Diabetic retinopathy (DR) is the most common cause of blindness in developed countries nowadays. It is the result of the increase in diabetes prevalence in those countries. According to WHO in the year 2002 diabetic retinopathy was the cause of blindness in 1.8 million people (4.8%) worldwide. In USA, every year, it becomes the reason for the loss of vision for about 12-24 thousand patients suffering from diabetes. From a clinical point of view DR has few variants, such as non-proliferative retinopathy, pre-proliferative retinopathy, diabetic maculopathy, proliferative retinopathy and advanced diabetic retinopathy. In most of these cases edema of the retina occurs and, in case of proliferative forms, proliferation of pathological blood vessels.

Age-related macular degeneration (AMD) is the main reason of the loss of vision in adults over 50 years old. It occurs in 8.8% of the population, more frequently in females, its occurrence increases with age and it affects almost 28% of people over age 75. It affects 50 million people globally. Due to population ageing the problem of AMD increases and about 10% of people over 45 years old are endangered by the disease. The so-called dry form of AMD makes up 90% of AMD cases and causes atrophic lesions within the macula and gradual loss of vision. In 10% of patients with AMD the wet (exudative) AMD form occurs, which causes blood vessel carcinogenesis in retina and choroid (choroidal neovascularization; CNV) and leads to a rapid vision worsening or vision loss.

Retinal artery occlusion, or its branch occlusion, is a relatively rare condition. It is characterized by a rapid and pain-less loss of vision. In case of quick treatment, a complete or partial recovery of the vision is achieved. One of the complications of the central retinal artery occlusion is the proliferation of pathological blood vessels in eye tissues.

Retinal vein occlusion occurs when the central retinal vein (central retinal vein occlusion—CRVO) or its branch (branch retinal vein occlusion—BRVO) is blocked. It leads to different kinds of vision degradation. CRVO and BRVO are the second most common vascular diseases of the retina. The form with ischemia is less common than the form without it. Retinal vein occlusions occur with an incidence of about 2 cases per 1000 people over 40 years of age and more than 5 cases per 1000 people over 64 years of age. As with central retinal artery occlusion, in cases of retinal vein occlusion late complications are possible, involving carcinogenesis of pathological blood vessels in the retina and in other eye tissues e.g. in drainage angle or iris.

Function of the Vascular Endothelial Growth Factor (VEGF) in the Increase in Permeability of Blood Vessels and Angiogenesis of Blood Vessels VEGF is a group of cytokines comprising a group of substances that include: VEGF-A, VEGF-B, VEGF-C, VEGF-D, VEGF-E, VEGF-F and PIGF (placental growth factor). The VEGF cytokines act through specific receptors. Currently a few of types thereof are known such as: VEGFR-1, VEGFR-2, FLK-1 and VEGFR-3. VEGF binds with receptors, which triggers a cascade of chemical reactions, which finally lead to an increase in permeability of blood vessels and stimulation of proliferation and migration of epithelial cells of blood and lymphatic vessels. Migrating cells of the endothelium create tubular structures, which are the buds of new blood vessels.

Secretion of VEGF is stimulated by many factors. These include pro-inflammatory cytokines, such as interleukin 1 (IL-1) and interleukin 6 (IL-6), substances secreted by tissues during the course of hypoxia e. g. hypoxia-induced factor (HIF-1), other growth factors e. g. transforming growth factor (TGF), insulin-like growth factor (IGF), fibroblast growth factor (FGF) and platelet-derived growth factor (PDGF).

The process of angiogenesis in eye tissues occurs mostly in low-oxygen supply conditions due to e. g. a decrease in blood flow or an increase in tissue demand for oxygen and in chronic tissue inflammation, when factors promoting secretion of VEGF are released. The blood vessels that are created in that way are responsible for the occurrence, inter alia, of collateral circulation in cardiac muscle, which plays a very important role in supporting correct tissue oxidation. Unfortunately, newly created blood vessels are not always beneficial for functioning of organs. For example, in the case of eye tissues, there occurs a pathological growth of blood vessels and breakdown of blood-retinal barrier, which in normal conditions prevents excessive penetration of fluid from blood vessels to tissues.

Function of the Vascular Endothelial Growth Factor (VEGF) in the Increase in Permeability of Blood Vessels and Angiogenesis of Blood Vessels in Eye Tissues An increase in secretion of VEGF occurs in diabetic retinopathy (proliferative and pre-proliferative), wet age-related macular degeneration, central retinal artery occlusion, central (or branch) retinal vein occlusion. The released VEGF increases permeability of blood vessels, which leads to breakdown of blood-retinal barrier, increase of in penetration of fluid to the retina and edema thereof. An increase in intra-tissue pressure in the retina causes breakdown of tissue and atrophy thereof. VEGF also stimulates formation of new vessels, which are characterized by high permeability, which further increases edema of surrounding tissues.

Newly created blood vessels disturb the physiological layout and course of blood vessels in the retina and the choroid of the eye and grow into vessel-free spaces e. g. the vitreous body. The walls of blood vessels formed during angiogenesis are fragile, they often break and cause hemorrhages into the vitreous body.

Currently, in order to decrease the edema of eye tissues and to inhibit angiogenesis inhibitors of VEGF or its receptors are used, such as ranibizumab (recombinant humanized monoclonal antibody fragment against VEGF-A), bevacizumab (recombinant humanized monoclonal antibody against VEGF-A) and aflibercept (Fc fragment of a receptor for VEGF). They are administered as repeated intravitreal injections, usually with one or two month intervals. The injection form of administration of the VEGF inhibitors requires sterile administration conditions, limits the number of potential patients and has a high risk of side effects.

Therefore, there is still a need for development of new means for treatment of eye diseases caused by an elevated level of vascular endothelial growth factor (VEGF), which would be effective and easily available, and their way of administration would be easier.

SUMMARY OF THE INVENTION

In order to find the solution for this problem the inventor of the present invention has conducted extensive research and has unexpectedly found that agonists of the type-2 dopaminergic receptors may be useful in treatment of eye diseases caused by an elevated level of vascular endothelial growth factor (VEGF), particularly in treatment or prevention of diseases of eye tissues, resulting from an increase in permeability of blood vessels and their carcinogenesis. Additionally, the inventor has found that the most preferred agonist of a dopaminergic D2 receptor is cabergoline.

Thus, the present invention relates to a use of type2 dopaminergic receptor agonists such as cabergoline in treatment of eye diseases caused by an elevated level of VEGF in eye tissues, which leads to their edema and to formation of pathological blood vessels.

The invention thus relates to a use of cabergoline and other agonists of a dopaminergic D2 receptor in treatment of eye diseases caused by an elevated level of vascular endothelial growth factor.

The present invention also relates to a possibility of using cabergoline and other agonists of a dopaminergic D2 receptor in treatment of eye diseases caused by an elevated level of vascular endothelial growth factor, in particular of diseases of an eye retina caused by an increase in permeability of blood vessels and/or their angiogenesis.

The invention also relates to a pharmaceutical composition containing as an active ingredient cabergoline or other agonists of a dopaminergic D2 receptor for use in treatment of eye diseases caused by an elevated level of vascular endothelial growth factor, in particular diseases of an eye retina caused by an increase in permeability of blood vessels and/or their carcinogenesis.

Preferably, the composition according to the invention is for oral administration.

DESCRIPTION OF THE INVENTION

Function of Dopaminergic D2 Receptors in Inhibition of VEGF Effects

It has been shown in experimental research that dopamine acting through dopamine D2 receptors inhibits permeability of blood vessels and proliferation and migration of vascular endothelial cells. This activity is presumably achieved by decreasing the number of VEGF-2 receptors and a decrease in affinity of VEGF-2 receptors to VEGF. The above observations are supported by clinical data. The agonist of dopaminergic D2 receptors—cabergoline is successfully used in prevention and treatment of ovarian hyperstimulation syndrome (OHSS). OHSS is related to an increased VEGF secretion by granulosa cells of an ovarian follicle due to hormonal stimulation of ovulation and to an increase in blood vessel permeability resulting from activation of the VEGF-2 receptor.

Pharmacological Effects of Dopaminergic D2 Receptor Agonist—Cabergoline

Cabergoline, having a structure according to the formula shown below, is a dopaminergic D2 receptor agonist.

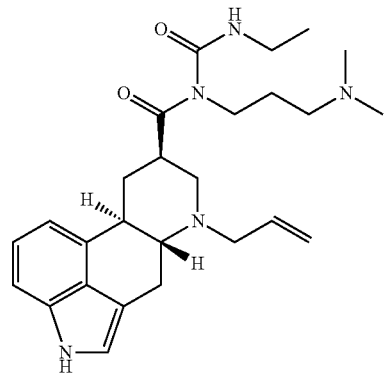 [SMILES: C=CCN1C[C@H](C(=O)N(CCCN(C)C)C(=O)NCC)C[C@@H]2c3cccc4[nH]cc(c34)C[C@H]21]

Cabergoline is used in treatment of disorders related to an excessive prolactin secretion (e. g. menstrual disorders, lack of ovulation, galactorrhea), pituitary adenoma, idiopathic hyperprolactinemia, empty sella syndrome. Cabergoline is used in treatment of the above mentioned disorders in doses from 0.5 mg once per day or from 0.25 mg to 4.5 mg once per week. Cabergoline is successfully used in prevention and treatment of OHSS as well, with a daily dose of 0.5 mg-1 mg over 7-14 days since the stimulation of ovulation.

Polish patent application P.343593 relates to use of cabergoline in treatment of a restless legs syndrome, while in polish patent applications P.344574, P.380898 and P.383475 use of cabergoline in combination with pramipexole for treatment of multiple systems atrophy, progressive supranuclear palsy and Parkinson's disease were described.

Example 1

The Effects of Administration of Cabergoline on Permeability of Blood-Retinal Barrier and on Retinal Thickness in an Experimental Model for Diabetic Retinopathy The research was conducted on an experimental model of Wistar strain rats. In order to cause diabetes, the rats were injected intraperitoneally with streptozocin at a dose of 60 mg/kg b.w. After 30 days since administration of streptozocin blood glucose level was checked and only rats with the blood glucose levels of over 250 mg % were qualified for the experiment.

In the course of the experiment, the following parameters were assessed: permeability of blood-retinal barrier using the dextran method (BRB) and the thickness of the retina using optical coherence tomography (OCT).

In the experiment, 4 experimental groups were compared: healthy animals without cabergoline administration, healthy animals with cabergoline administration (14 days of use), animals with diabetes without cabergoline, animals with diabetes with cabergoline (14 days of use). Cabergoline was administered to the animals in oral form at a dose of 0.05 mg/kg b.w. over 14 days.

| Experimental group/Parameter | BRB (μl/g/min) | OCT (μm) |
|---|---|---|
| Control group | 25.6 ± 4.5 | 272 ± 10 |
| Group with diabetes without cabergoline | 54.6 ± 12.1 | 383 ± 29 |
| Healthy group with cabergoline | 22.4 ± 7.5 | 281 ± 14 |
| Group with diabetes with cabergoline | 35.8 ± 10.6 | 320 ± 35 |

Example 2

The Effects of Administration of Cabergoline on Permeability of Blood-Retinal Barrier and Retinal Thickness in an Experimental Model for Central Retinal Vein Occlusion.

The research was conducted on an experimental model of Wistar strain rats. Central retinal vein occlusion was performed using a 532 nm laser.

In the course of the experiment, the following parameters were assessed: permeability of blood-retinal barrier using the dextran method (BRB) and the thickness of the retina using optical coherence tomography (OCT).

In the experiment, 4 experimental groups were compared: healthy animals without cabergoline administration, healthy animals with cabergoline administration (14 days of use), animals with central retinal vein occlusion without cabergoline, animals with central retinal vein occlusion with cabergoline (14 days of use). Cabergoline was administered to the animals in oral form at a dose of 0.05 mg/kg b.w. over 14 days.

| Experimental group/Parameter | BRB (μl/g/min) | OCT (μm) |
|---|---|---|
| Control group | 23.2 ± 6.8 | 235 ± 14 |
| Group with central retinal vein occlusion without cabergoline | 48.9 ± 14.6 | 419 ± 36 |
| Healthy group with cabergoline | 25.1 ± 4.2 | 258 ± 13 |
| Group with central retinal vein occlusion with cabergoline | 33.3 ± 12.9 | 343 ± 28 |

Example 3

The Effects of Administration of Cabergoline on Permeability of Blood-Retinal Barrier and Retinal Thickness in an Experimental Model for Choroidal Neovascularization (CNV).

The research was conducted on an experimental model of Wistar strain rats. Choroidal neovascularization (CNV) was performed by photocoagulation of the retina using a 532 nm laser.

In the course of the experiment, the following parameters were assessed: permeability of blood-retinal barrier using the dextran method (BRB) and the thickness of the retina using optical coherence tomography (OCT).

In the experiment, 4 experimental groups were compared: healthy animals without cabergoline administration, healthy animals with cabergoline administration (14 days of use), animals with CNV without cabergoline, animals with CNV with cabergoline (14 days of use). Cabergoline was administered to the animals in oral form at a dose of 0.05 mg/kg b.w. over 14 days.

| Experimental group/Parameter | BRB (μl/g/min) | OCT (μm) |
|---|---|---|
| Control group | 27.3 ± 9.2 | 242 ± 28 |
| Group with CNV without cabergoline | 43.1 ± 9.9 | 362 ± 32 |
| Healthy group with cabergoline | 28.5 ± 6.6 | 221 ± 22 |
| Group with CNV with cabergoline | 37.4 ± 15.2 | 283 ± 17 |

The invention claimed is:

1. A method for treating an eye disease associated with an elevated level of vascular endothelial growth factor, the method comprising administering to a patient who has an eye disease associated with an elevated level of vascular endothelial growth factor a pharmaceutical composition comprising a therapeutically-effective amount of Cabergoline.

2. The method according to claim 1 wherein the pharmaceutical composition comprising Cabergoline is administered orally.

3. The method according to claim 1 wherein the eye disease is a disease of an eye retina resulting from an increase in permeability of blood vessels and/or their angiogenesis.

4. The method according to claim 1 wherein the eye disease being treated is diabetic macular edema, diabetic retinopathy, age-related macular degeneration, retinal artery occlusion, retinal vein occlusion or choroidal neovascularization.

5. The method according to claim 4 wherein the eye disease being treated is diabetic retinopathy, retinal vein occlusion or choroidal neovascularization.

6. The method according to claim 2 wherein the eye disease is a disease of an eye retina resulting from an increase in permeability of blood vessels and/or their angiogenesis.

7. The method according to claim 2 wherein the eye disease being treated is diabetic macular edema, diabetic retinopathy, age-related macular degeneration, retinal artery occlusion, retinal vein occlusion or choroidal neovascularization.

8. The method according to claim 7 wherein the eye disease being treated is diabetic retinopathy, retinal vein occlusion or choroidal neovascularization.

* * * * *